(12) United States Patent
Skubitz et al.

(10) Patent No.: US 10,541,500 B2
(45) Date of Patent: Jan. 21, 2020

(54) CONNECTOR CONSTRUCTIONS AND COMPONENTS THEREOF FOR IMPLANTABLE MEDICAL ELECTRICAL SYSTEMS

(71) Applicant: Medtronic, Inc., Minneapolis, MN (US)

(72) Inventors: Sean P. Skubitz, Forest Lake, MN (US); Daniel C. Oster, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 266 days.

(21) Appl. No.: 15/678,542

(22) Filed: Aug. 16, 2017

(65) Prior Publication Data
US 2019/0058297 A1  Feb. 21, 2019

(51) Int. Cl.
| | | |
|---|---|---|
| *H01R 24/58* | (2011.01) | |
| *A61N 1/05* | (2006.01) | |
| *H01R 13/44* | (2006.01) | |
| *H01R 13/03* | (2006.01) | |

(52) U.S. Cl.
CPC .............. *H01R 24/58* (2013.01); *A61N 1/05* (2013.01); *H01R 13/44* (2013.01); *H01R 13/03* (2013.01); *H01R 2201/12* (2013.01)

(58) Field of Classification Search
CPC ............................... A61N 1/3752; H01R 24/58
See application file for complete search history.

(56) References Cited

U.S. PATENT DOCUMENTS

| | | | |
|---|---|---|---|
| 6,895,276 B2 | 5/2005 | Kast et al. | |
| 8,131,370 B2 | 3/2012 | Janzig et al. | |
| 8,167,660 B2 | 5/2012 | Dilmaghanian et al. | |
| 8,480,437 B2 | 7/2013 | Dilmaghanian et al. | |
| 8,567,055 B2 | 10/2013 | Fan et al. | |
| 8,712,527 B2 | 4/2014 | Seeley et al. | |
| 9,421,362 B2 | 8/2016 | Seeley | |
| 9,472,916 B2 | 10/2016 | Hanson et al. | |
| 2005/0272280 A1* | 12/2005 | Osypka ................. | A61N 1/056 439/71 |
| 2011/0106189 A1* | 5/2011 | Seeley ................. | A61N 1/3752 607/2 |
| 2014/0273623 A1* | 9/2014 | Hanson ................. | H01R 43/20 439/587 |

* cited by examiner

*Primary Examiner* — George R Evanisko
(74) *Attorney, Agent, or Firm* — Shumaker & Sieffert, P.A.

(57) ABSTRACT

A connector assembly, for example, employed in an extension of an implantable medical electrical system, may be contained in a flexible insulative sleeve so that a bore thereof extends along a longitudinal axis of the sleeve with an opening being formed by a distal terminal end of the sleeve. The assembly includes a plurality of isolation ring components interspersed among a plurality of contact ring components, wherein each of a plurality of conductor components has a first end coupled to a corresponding contact ring component, and a curvature formed along a length thereof, which length extends proximally from the coupled first end and into a proximal portion of the sleeve. To facilitate routing of the conductor component lengths, either each isolation ring component may include at least one guide, or a flexible inner insulative sleeve of the assembly may have longitudinally extending channels formed in an outer surface thereof.

20 Claims, 9 Drawing Sheets

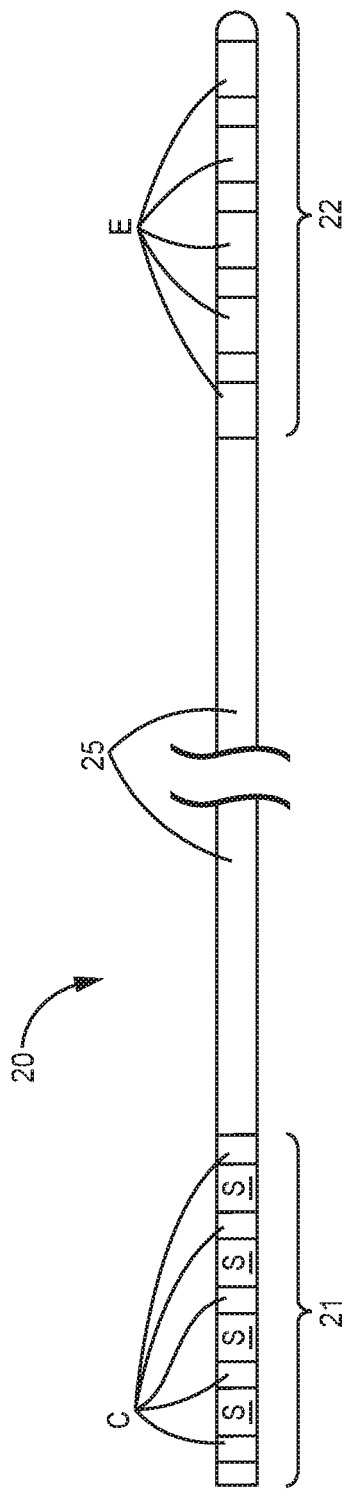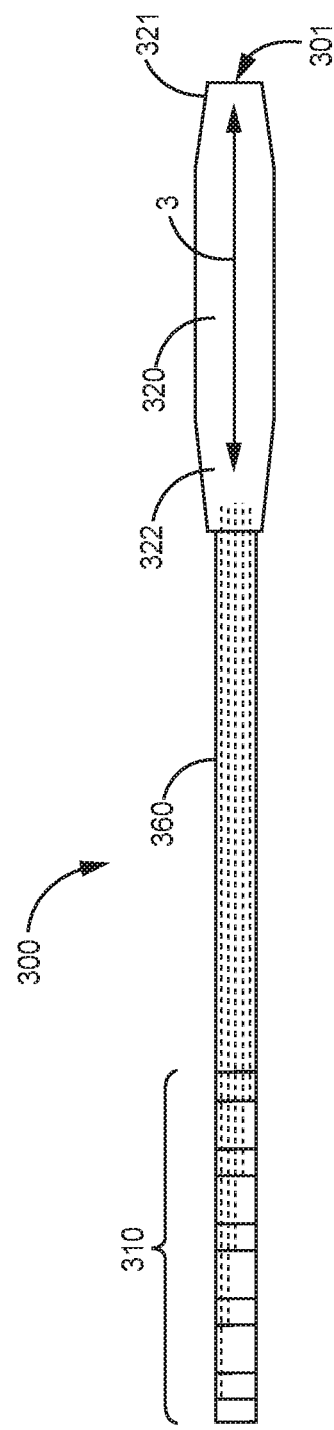

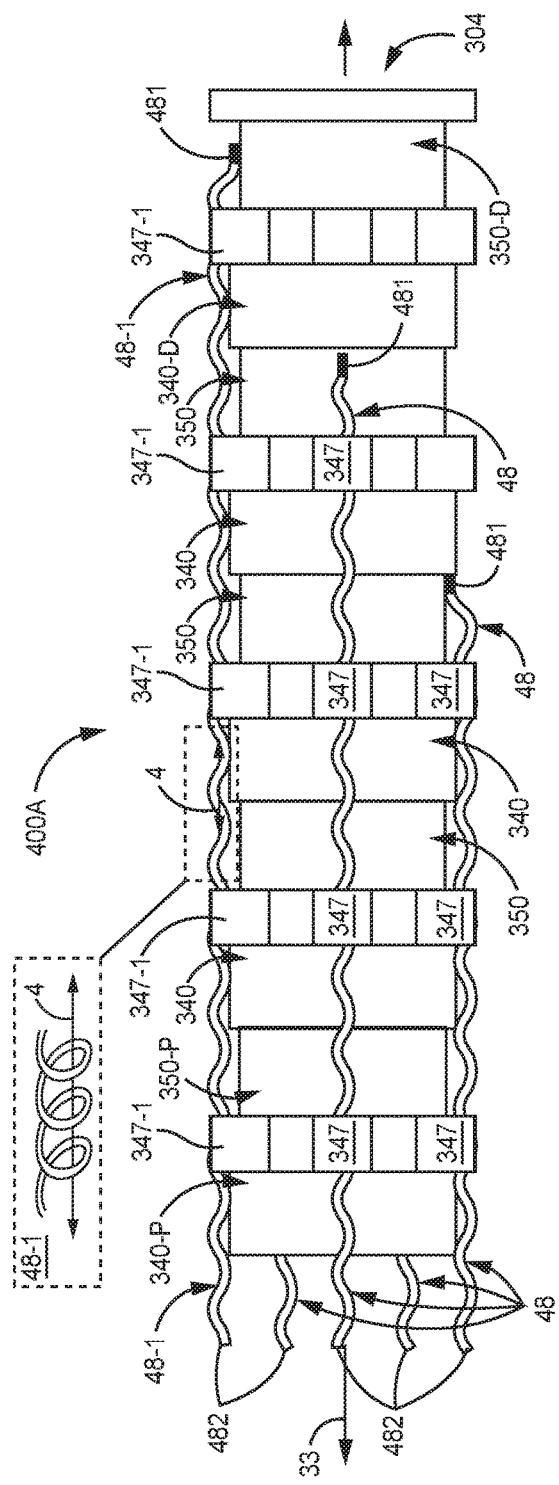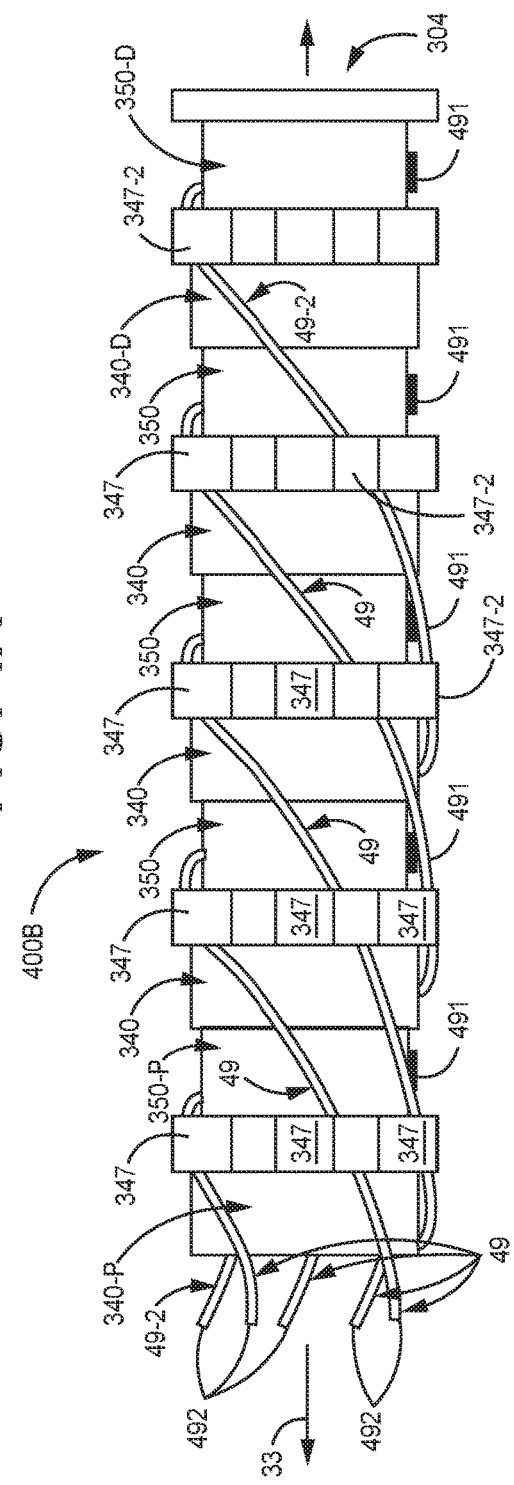
FIG. 4A
FIG. 4B

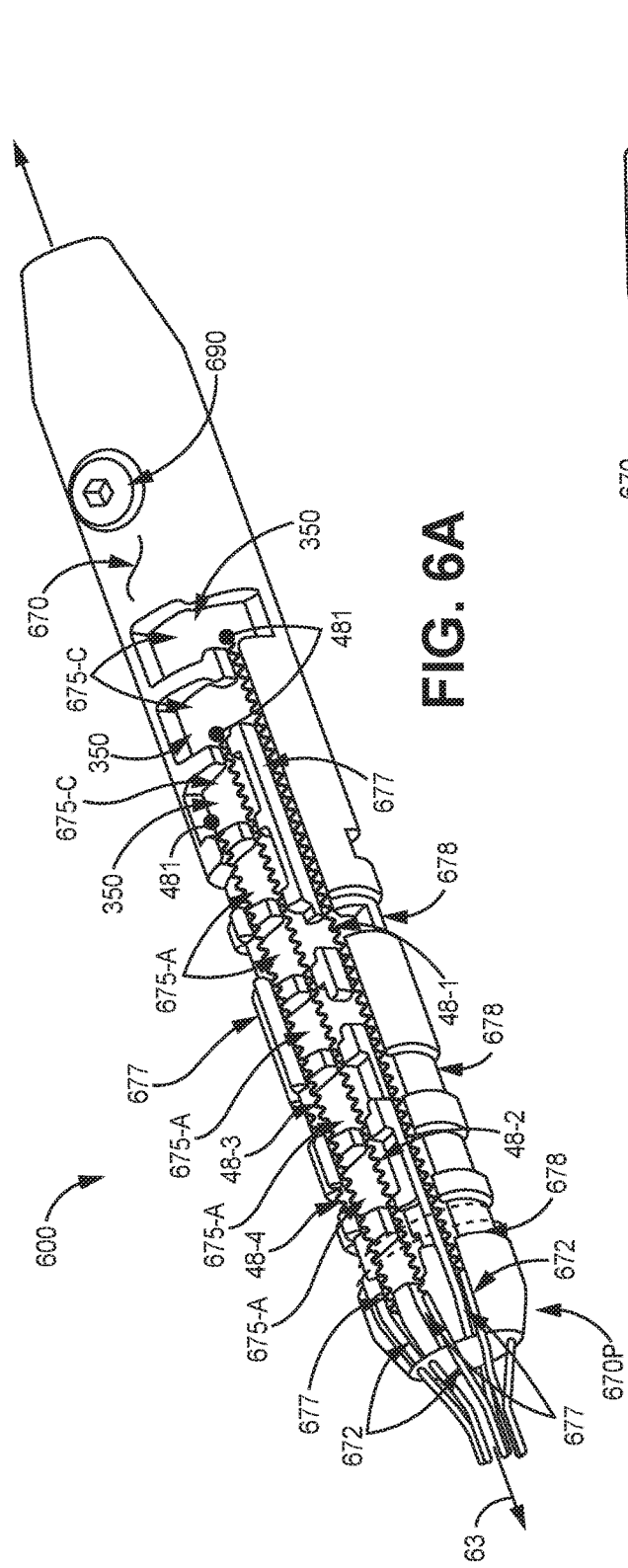
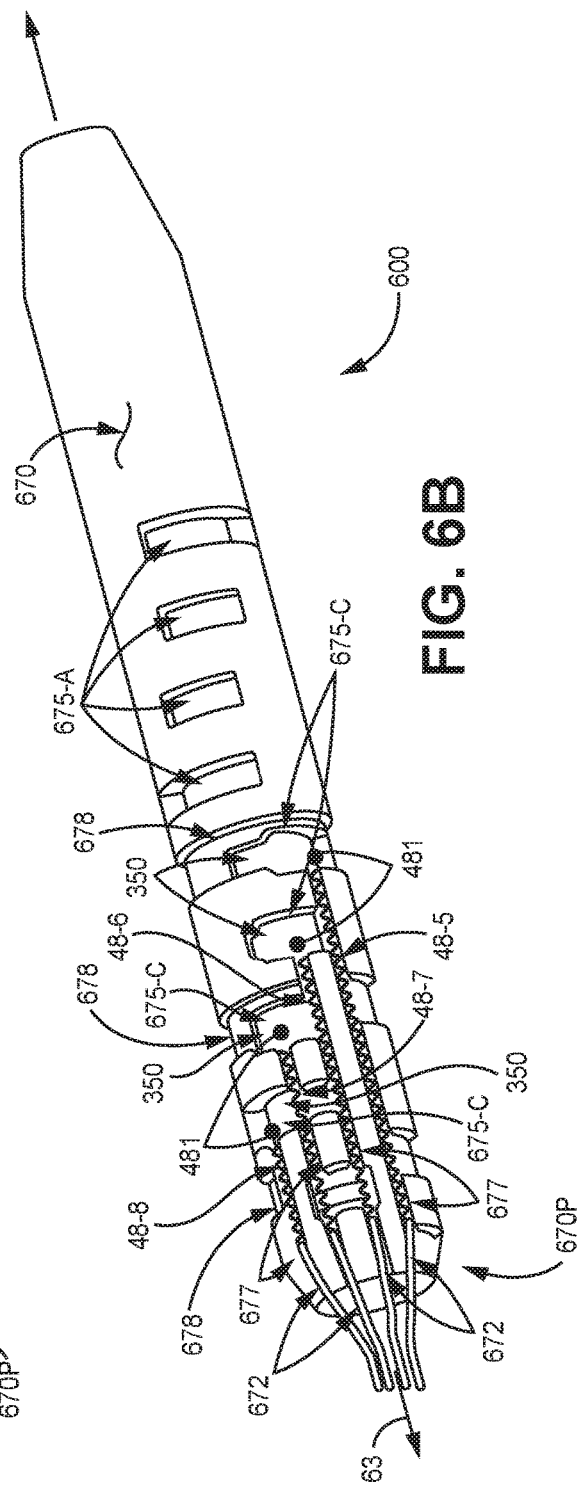

CONNECTOR CONSTRUCTIONS AND COMPONENTS THEREOF FOR IMPLANTABLE MEDICAL ELECTRICAL SYSTEMS

TECHNICAL FIELD

The present disclosure is related to implantable medical electrical systems, and more particularly to constructions and components of connectors that may convert and/or extend an implantable medical electrical lead for coupling to an implantable medical electrical device.

BACKGROUND

Implantable medical devices are commonly used to treat conditions such as cardiac arrhythmias, pain, incontinence, sleep disorders, and movement disorders such as Parkinson's disease and epilepsy. One type of implantable medical device, a neurostimulator, delivers mild electrical impulses to neural tissue through an array of electrodes mounted to an implantable medical electrical lead. Typically, such a device and lead are part of totally implantable stimulation system that may be controlled by a physician or a patient through the use of an external programmer connected to the device, for example, via telemetry, wherein the device generally includes a power source and a pulse generator contained in a hermetically sealed enclosure. This type of system also often includes an extension configured to facilitate electrical coupling of the lead to the device.

FIG. 1 is a schematic showing an exemplary deep brain stimulation system, implanted in a patient. FIG. 1 illustrates an implantable medical device 60 of the system being implanted in pectoral region of a patient, and an implantable medical electrical lead 20 of the system being electrically coupled to device 60 via an extension 30, and extending distally therefrom through a burr hole 10 formed in the patient's cranium where an electrode array of lead 20 (not shown) is positioned at a target stimulation site. Extension 30 includes a distal, female connector 32 coupled to a proximal terminal connector of lead 20, and a proximal male connector 31 coupled to device 60, for example, being plugged into a bore of a connector module thereof.

BRIEF SUMMARY

A medical device may comprise a female connector assembly, which may be used, in one example, on a lead extension. The female connector may be contained in an insulative sleeve, such as a sleeve of a lead extension, so that an opening of a bore of the assembly is formed by a distal terminal end of the sleeve, the bore defining a longitudinal axis of the assembly. According to embodiments disclosed herein, such a female connector assembly includes a plurality of isolation ring components interspersed between a plurality of contact ring components of the assembly, and plurality of conductor components, wherein each conductor component has a first end coupled to an outer surface of a corresponding contact ring component, and a curvature formed along a length thereof (e.g., a repeating sigmoid or a helix), which length extends proximally from the coupled first end, and may extend through a guide channel of the assembly.

According to some embodiments, a guide of each isolation ring component, through which the aforementioned channel is formed, extends outward from an outer surface of the corresponding isolation ring component, and each isolation ring component further includes a seal lip extending into the bore, being defined by an inner surface of the corresponding isolation ring component. According to some alternate embodiments, the isolation ring components do not include guides, and in some of these embodiments a flexible inner insulation sleeve, which extends around the isolation ring and contact ring components, having an inner surface in intimate contact with each, includes a plurality of longitudinally extending channels formed in an outer surface thereof to facilitate the routing of the conductor components.

In an extension that employs any of the above-described assemblies, according to some embodiments, each of the plurality of conductor components is an integral extension of a corresponding elongate insulated conductor that extends within a body of the extension. In some alternate embodiments of extensions that include the assembly with the inner insulative sleeve, a coupling between each of the plurality of conductor components and a corresponding elongate insulated conductor is located in one of the channels at a proximal end of the inner insulative sleeve.

In one embodiment, a medical system comprises an implantable device coupled to the sleeve carrying the connector system according to embodiments described above.

BRIEF DESCRIPTION OF THE DRAWINGS

The following drawings are illustrative of particular embodiments and do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 2 is a plan view of an implantable medical electrical lead, according to an exemplary embodiment, which may be employed by the system of FIG. 1;

FIG. 3A is a plan view of an extension, according to some embodiments, which may be employed to extend and/or convert the lead of FIG. 2 for coupling to an implantable medical device;

FIG. 4A is a plan view of a female connector assembly, according to an embodiment in a first group of embodiments;

FIG. 4B is a plan view of a female connector assembly, according to an alternate embodiment from the first group of embodiments;

FIGS. 6A-B are two perspective views of another alternate embodiment from the first group of female connector assembly embodiments.

DETAILED DESCRIPTION

The following detailed description is exemplary in nature and is not intended to limit the scope, applicability, or configuration of inventive embodiments disclosed herein in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1:
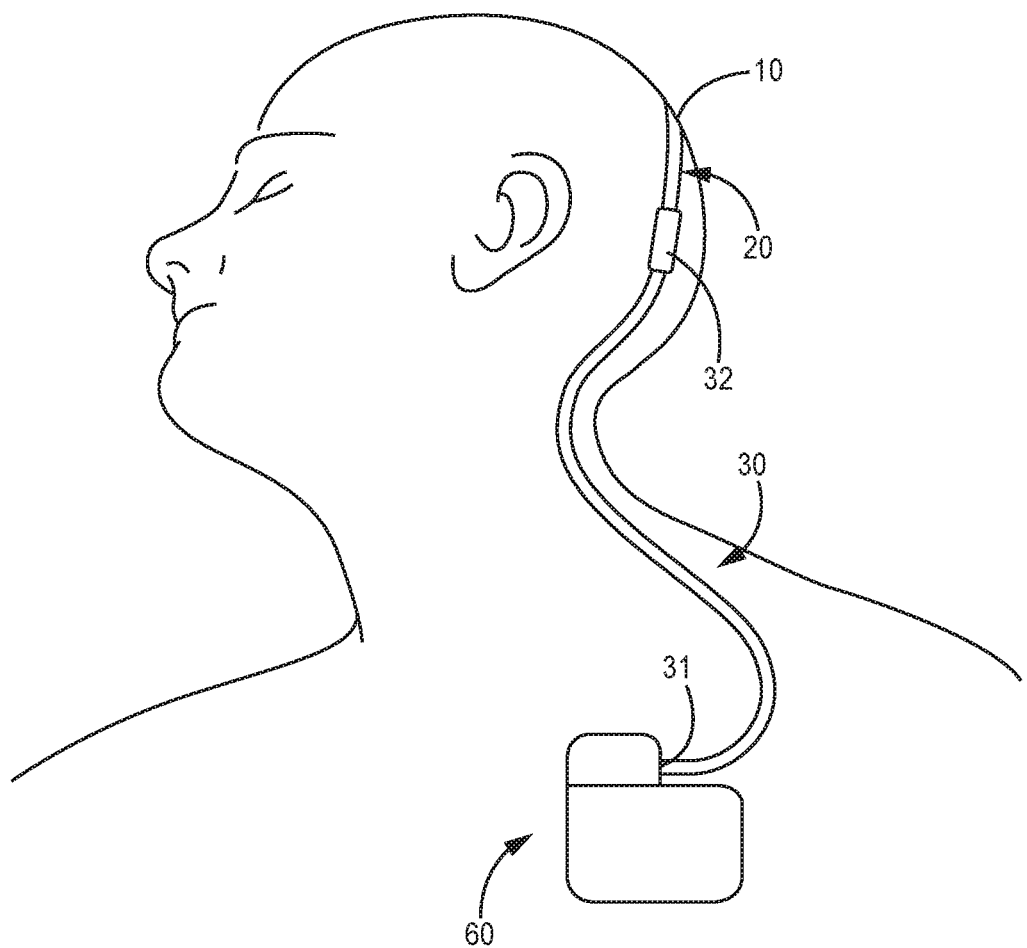
FIG. 1 is a schematic showing an exemplary stimulation system implanted in a patient.
Figure 3B:
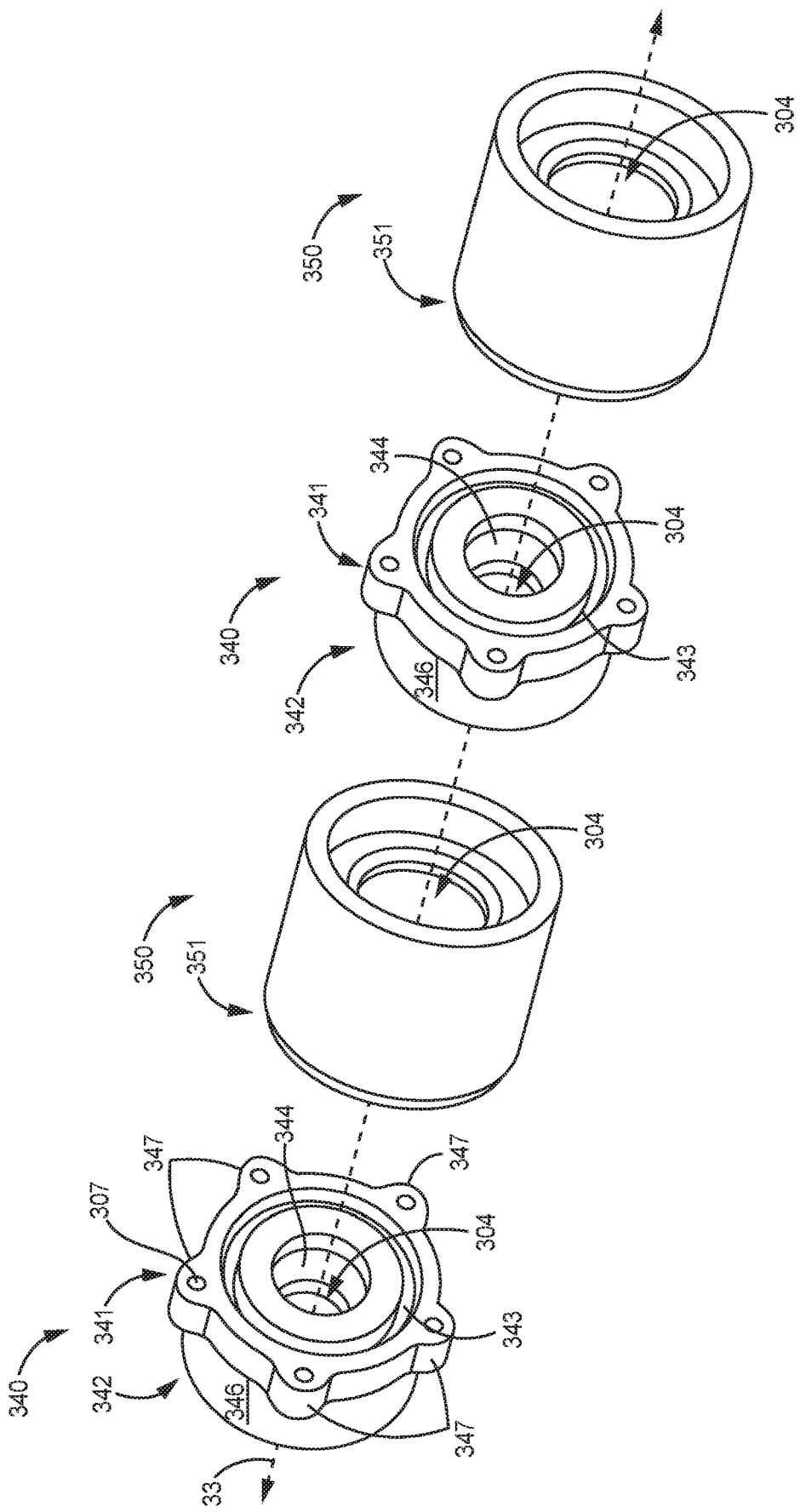
FIG. 3B is an exploded perspective view of a portion of a female connector assembly of the extension, according to some embodiments.

FIG. 2 is a plan view of the aforementioned medical electrical lead 20, according to an exemplary embodiment; and FIG. 3A is a plan view of an extension 300, according to some embodiments, which may be employed to couple lead 20 to an implantable medical device, for example, device 60 in lieu of the aforementioned extension 30 (FIG. 1). FIG. 2 illustrates lead 20 including an elongate body 25 that extends distally from a proximal terminal connector 21 of lead 20 to an electrode array 22 of lead 20. FIG. 2 further illustrates terminal connector 21 including a plurality of contact surfaces C spaced apart and isolated from one another by a plurality of insulative spacers S, and electrode array 22 including a plurality of electrodes E spaced apart and isolated from one another. Those skilled in the art understand that a plurality of elongate insulated conductors, being electrically isolated from one another, extend along body 25, from terminal connector 21 to electrode array 22, in order to electrically couple each electrode E to a corresponding contact surface C. FIG. 3A illustrates extension 300 also including an elongate body 360, in which a plurality of elongate insulated conductors, for example, in the form of cables or coils, extend. In FIG. 3A the elongate insulated conductors are indicated with dashed lines, but it should be noted that these conductors may be wound as a single coil around a common longitudinal axis. Extension 300 is shown terminated, at a proximal end thereof, by a male connector assembly 310, and, at a distal end thereof, by an insulative sleeve 320, which is preferably formed from a medical grade silicone rubber or the like. According to the illustrated embodiment, sleeve 320 contains a female connector assembly that has a bore defining a longitudinal axis of the connector assembly (e.g. bore 304 and axis 33 of FIG. 3B, or bore 604 of FIG. 6C), wherein the bore extends along a longitudinal axis 3 of sleeve 320 and a distal terminal end 321 of sleeve 320 defines an opening 301 into the bore. The aforementioned elongate insulated conductors electrically couple the female connector assembly to male connector assembly 310. Each of the conductors may be formed from the MP35N alloy, known in the art, and have an insulative coating such as a polyamic acid coating, or an over-extruded layer of a medical grade fluoropolymer, such as ethylene tetrafluoroethylene. The connector assembly bore is sized to receive insertion of lead terminal connector 21 therein so that male connector assembly 310 of extension 300, when plugged into a connector module of an implantable medical device, such as device 60, electrically couples the inserted terminal connector 21 to the device. A relative flexibility of the female connector assembly contained within sleeve 320 is desirable to generally match that of a length of extension 300 between male connector assembly 310 and distal terminal end 321. Various female connector assembly embodiments that can be incorporated into extension 300 are described below, starting with FIG. 3B.

FIG. 3B is a perspective view some components, in particular, a plurality of isolation ring components 340 and a plurality of contact ring components 350, according to some embodiments, of the various female connector assembly embodiments, exploded along a longitudinal axis 33 defined by a bore 304 the assembly. FIG. 3B illustrates each isolation ring component 340 including an inner surface that defines a corresponding portion of female connector assembly bore 304, and a seal lip 344 that extends into bore 304 far enough to touch contacts C as lead terminal connector 21 (FIG. 2) is inserted into bore 304. According to an exemplary embodiment, each seal lip 344 has an aspect ratio of less than 1. Each portion of bore 304 extends along longitudinal axis 33, from a first end 341 of component 340 to a second end 342 of component 340. FIG. 3B further illustrates each contact ring component 350, which also extends around bore 304 and along longitudinal axis 33, being positioned adjacent a corresponding isolation ring component 340 for engagement of an end 351 thereof with a face of the corresponding isolation ring component first end 341. According to some embodiments, as shown, the face of isolation ring component first end 341 may have an annular groove 343 formed therein to engage end 351 of contact ring component 350; but according to some alternate embodiments, first end 341 may be defined by a relatively flat surface. According to the illustrated embodiment, and with reference back to FIGS. 2 and 3A, when isolation ring components 340 and contact ring components 350 are engaged together along longitudinal axis 33 and within insulative sleeve 320 of extension 300, and when lead terminal connector 21 is fully inserted into bore 304 via opening 301 of sleeve 320, each seal lip 344 is located to seat on, and seal against, a corresponding insulative spacer S, and an inner contact surface of each contact ring component 350 is located to seat on a corresponding contact surface C. With reference to the cross-section view of contact ring component 350 shown in FIG. 3D, according to an exemplary embodiment, the inner contact surface of contact ring component 350 is formed by a coiled conductive spring 354, which is contained within a conductive housing 356 of contact ring component 350, according to constructions well known to those skilled in the art.

Figures 3C, 3D:
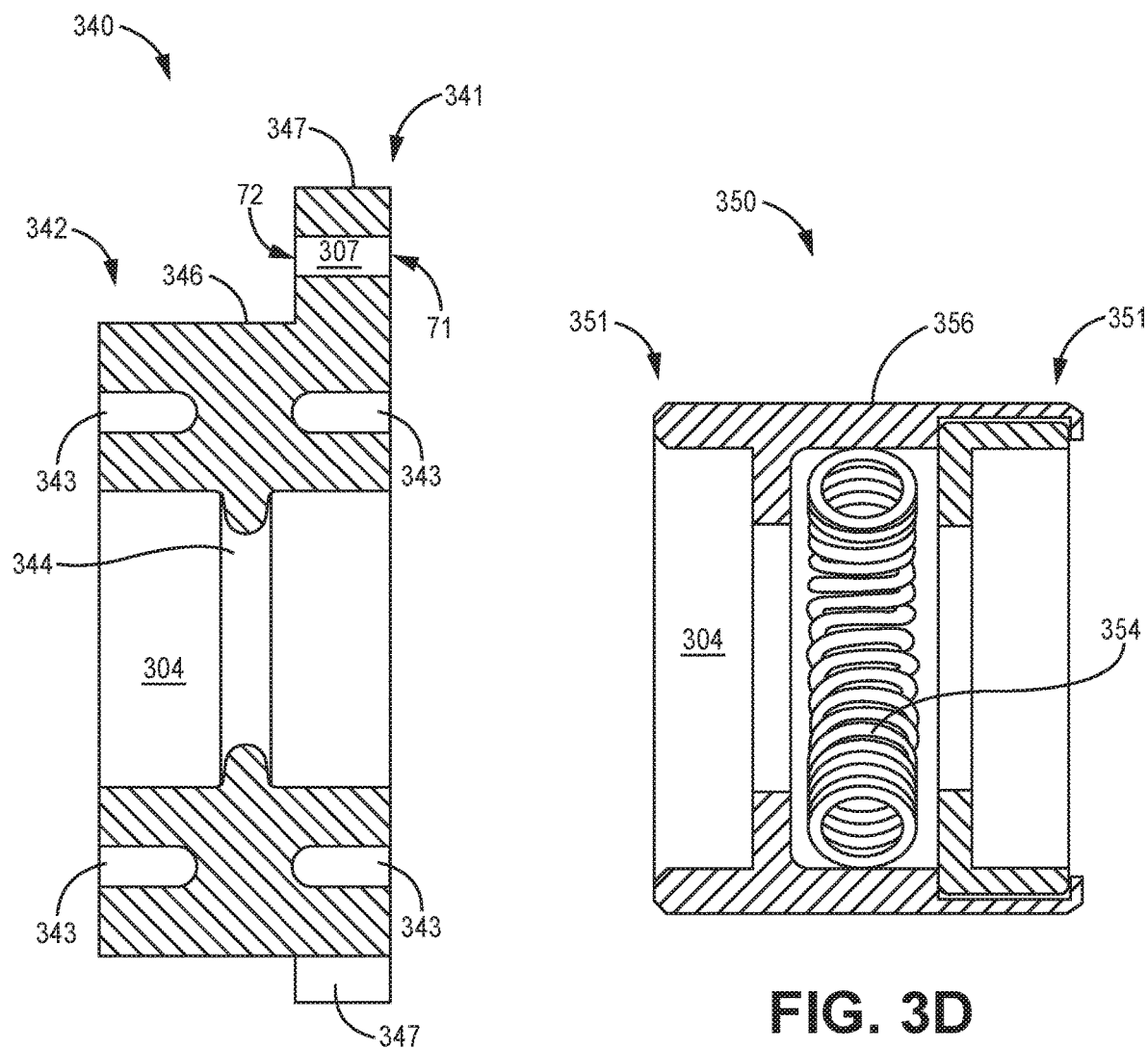
FIG. 3C is a cross-section view of an isolation ring component of the female connector assembly, according to some embodiments.
FIG. 3D is a cross-section view of a contact ring component of the female connector assembly, according to some embodiments.

With further reference to FIGS. 3B-C, each isolation ring component 340 of the various female connector assembly embodiments may include at least one guide 347 extending outward from an outer surface 346 thereof, wherein each guide 347 has a channel 307 formed therethrough. Guides 347 may be formed by a plurality of lobes circumferentially offset from one another around longitudinal axis 33, wherein each lobe has a corresponding channel 307 formed therethrough, as shown. FIG. 3C illustrates each guide channel 307 extending substantially parallel to longitudinal axis 33, from a first opening 71 thereof, for example, in proximity to the face of first end 341 of the corresponding isolation ring component 340, to a second opening 72 thereof, wherein each channel 307 is configured to receive therethrough passage of an elongate conductor component of the various female connector assembly embodiments, for example, as described below in conjunction with FIGS. 4A-5. According to some preferred embodiments, an entirety of isolation ring component 340 is formed from a medical grade silicone rubber, wherein guide(s) 347 and seal lip 344 are integrally formed. Thus, when sleeve 320 is also formed from silicone rubber, for example, being insert molded around any of the female connector assembly embodiments described herein, a durability and integrity of electrical isolation are ensured by coalescence of material at the interfaces between sleeve 320 and isolation ring components 340. According to some alternate embodiments, female connector assemblies may include isolation ring components without guides, for example, isolation ring components 640 of an assembly 600 described below in conjunction with FIGS. 6A-C.

FIGS. 4A-B are plan views of alternative female connector assemblies 400A, 400B, according to a first group of embodiments, which may be contained in insulative sleeve 320 of extension 300. FIGS. 4A-B illustrate each connector assembly 400A, 400B including isolation ring components 340 and connector ring components 350 engaged together along longitudinal axis 33, as described above. A proximal-most of contact ring components 350 and isolation ring components 340 are designated 350-P and 340-P, respectively, in each assembly 400A, 400B, wherein, when assembly 400A, 400B is contained within sleeve 320 (FIG. 3A), each is located within a proximal portion 322 thereof. A distal-most of contact ring components 350 and isolation ring components 340 are designated 350-D and 340-D, respectively, in each assembly 400A, 400B, and are located in proximity to distal terminal end 321 of sleeve 320, when assembly 400A, 400B is contained therein. FIGS. 4A-B further illustrate each assembly 400A, 400B including a plurality of conductor components 48, 49, wherein each conductor component 48, 49 has, formed along a length thereof, a curvature defined by a helix. The curvature of each component 48, 49 lends kink resistance (or strain relief) thereto along the lengths thereof, which may be particularly desirable for the aforementioned preferred embodiments in which isolation ring components 344 and sleeve 320 are both formed from a relatively flexible material like silicone rubber. According to some exemplary embodiments, conductor components 48, 49 may be formed from the MP35N alloy known to those skilled in the art, and may include an insulative coating such as a polyamic acid coating.

FIG. 4A illustrates each conductor component 48 of assembly 400A having a first end 481 coupled, for example, by a weld, to a corresponding contact ring component 350, wherein the length of each conductor component 48 extends proximally from the corresponding first end 481 and, according to some embodiments, through a corresponding guide 347 of one or more isolation ring components 340. According to some alternate embodiments, guides 347 are not included, and some of these embodiments include an alternative means for routing conductors 48, for example, like assembly 600 of FIGS. 6A-C. In either case, the length of each component extends substantially parallel to longitudinal axis 33. If guides 347 are included, as shown, those through which each of the majority of components 48 extends are aligned with one another along longitudinal axis 33, for example, the guides designated 347-1 and the corresponding conductor component designated 48-1. (First ends 481 of two of conductor components 48 are not visible in the plan view of FIG. 4A, so it should be understood that one of each of these ends 481 is coupled to proximal-most contact ring component 350-P and the other to the adjacent contact ring component 350, wherein the length of the former extends through one of guides 347 of proximal-most isolation ring component 340-P only, and the length of the latter extends through one of the guides 347 of the adjacent isolation ring component 340 and another guide 347 of proximal-most isolation ring component 340-P.) With further reference to FIG. 4A, in particular to the enlarged detail of a portion of conductor component 48-1, it can be understood that the aforementioned helix curvature of each conductor component 48 is coiled around a centerline, e.g. centerline 4, which is laterally offset from longitudinal axis 33.

FIG. 4B illustrates each conductor component 49 of assembly 400B having a first end 491 coupled, for example, by a weld, to a corresponding contact ring component 350, wherein the length of each conductor component 49 extends proximally from the corresponding first end 491 and, according to some embodiments, through a corresponding guide 347 of one or more isolation ring components 340. According to some alternate embodiments of assembly 400B, guides 347 are not included. In either case, the aforementioned helix curvature of each conductor component 49 extends around longitudinal axis 33. If guides 347 are included, as shown, those through which each of the majority of components 48 extend, are circumferentially offset from one another around longitudinal axis 33, for example, the guides designated 347-2 and the corresponding conductor component 49-2.

Figure 4C:
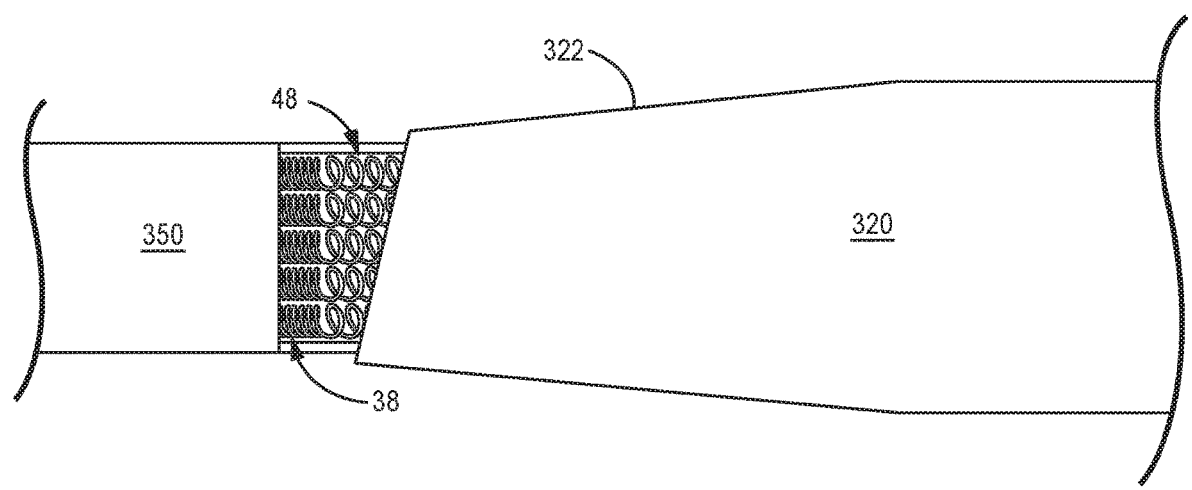
FIG. 4C is a cut-away section of a portion of the extension, according to some embodiments.

With further reference to FIGS. 4A-B, a distal end 482, 492 of each conductor component 48, 49 may be coupled to a corresponding elongate insulated conductor of the aforementioned plurality that extends within elongate body 360 of extension 300 (dashed lines in FIG. 3A), for example, via a conductive sleeve coupling, according to any suitable method known to those skilled in the art. But, in some alternate embodiments, each conductor component 48, 49 can be an integral extension of the corresponding elongate insulated conductor. In one example, shown in a cut-away section of FIG. 4C, each elongate insulated conductor and the corresponding integral extension that forms conductor component 48 is formed by a coiled wire, wherein a close-wound portion 38 of each coiled wire extends within elongate body 360, and a space-wound portion of each coiled wire defines the corresponding conductor component 48 of connector assembly 400A. In another example, for connector assembly 400B, each elongate insulated conductor and the corresponding integral extension that forms conductor component 49 is formed by a cabled bundle of wires, which may extend along a similar helical path within elongate body 360. And, in yet another example, each elongate insulated conductor may be wound as a single coil around a common longitudinal axis that extends along the length of elongate body 360, wherein each conductor component 48 is unwound from around the common axis and then wound around a corresponding centerline thereof, that is offset from axis 33 (e.g., centerline 4 of FIG. 4A).

Figure 5:
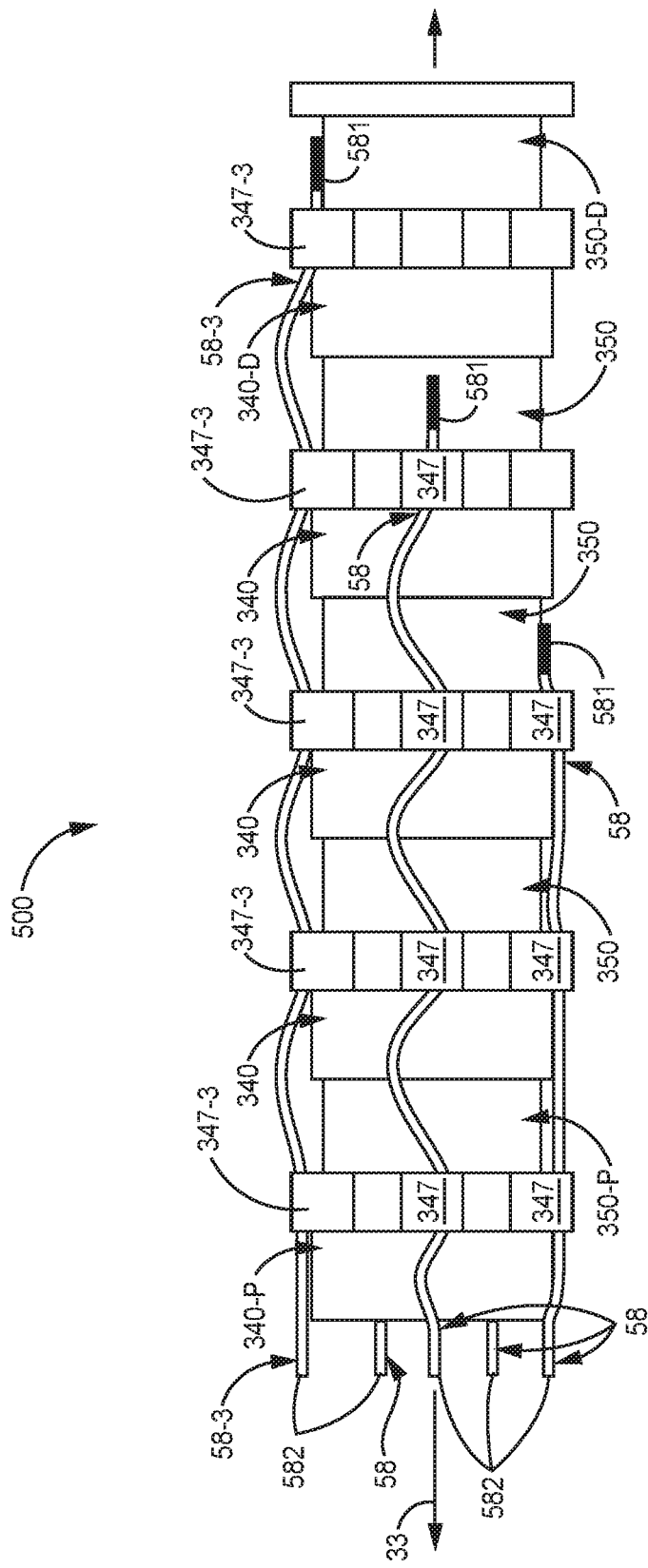
FIG. 5 is a plan view of a female connector assembly, according to an embodiment in a second group of embodiments.

FIG. 5 is a plan view of a female connector assembly 500, according to an embodiment in a second group of embodiments, which may be contained in insulative sleeve 320 of extension 300. FIG. 5 illustrates connector assembly 500 including contact ring components 350 and isolation ring components 340 engaged together along longitudinal axis 33, as described above, wherein the proximal-most of contact ring components 350 and isolation ring components 340 are designated 350-P and 340-P, respectively, and the distal-most of contact ring components 350 and isolation ring components 340 are designated 350-D and 340-D, respectively, the same as in assemblies 400A, 400B. FIG. 5 further illustrates connector assembly 500 including a plurality of conductor components 58, wherein each conductor component 58 has, formed along a length thereof, a curvature defined by a repeating sigmoid. The curvature of each component 58 lends kink resistance (or strain relief) thereto along the lengths thereof, which may be particularly desirable for the aforementioned preferred embodiments in which isolation ring components 344 and sleeve 320 are both formed from a relatively flexible material like silicone rubber. According to some exemplary embodiments, components 58 may be formed from the MP35N alloy known to those skilled in the art, and may include the insulative polyamic acid coating.

With further reference to FIG. 5, each conductor component 58 has a first end 581 coupled, for example, by a weld, to a corresponding contact ring component 350, wherein the length of each conductor component 58 extends proximally from the corresponding first end 581 and, according to some embodiments, through a corresponding guide 347 of one or more isolation ring components 340. According to some alternate embodiments of assembly 500, guides 347 are not included. In either case, like conductor components 48 of connector assembly 400A, the length of each conductor component 58 of assembly 500 extends substantially parallel to longitudinal axis 33, but, the repeating sigmoid curvature of conductor components 58 extends substantially in a single plane, being relatively flat, in contrast to the three-dimensional helical curvature of the coiled conductor components 48. If guides 347 are included, as shown, those through which each of the majority of components 58 extends are aligned with one another along longitudinal axis 33, for example, the guides designated 347-3 and the corresponding conductor component designated 58-3. (First ends 581 of two of conductor components 58 are not visible in the plan view of FIG. 5, so it should be understood that one of each of these ends 581 is coupled to proximal-most contact ring component 350-P and the other to the adjacent contact ring component 350, wherein the length of the former extends through one of guides 347 of proximal-most isolation ring component 340-P only, and the length of the latter extends through one of the guides 347 of the adjacent isolation ring component 340 and another guide 347 of proximal-most isolation ring component 340-P.)

A distal end 582 of each conductor component 58 may be coupled to a corresponding elongate insulated conductor of the aforementioned plurality that extends within elongate body 360 of extension 300 (dashed lines in FIG. 3A), for example, via a conductive sleeve coupling, according to any suitable method known to those skilled in the art. But, in some alternate embodiments, each conductor component 58 can be an integral extension of the corresponding elongated insulated conductor. In one example, similar to that described above in conjunction with FIG. 4C, each elongate insulated conductor may be formed by a coiled wire, wherein a distal portion of each coiled wire is re-formed into the repeating sigmoid curvature to form the corresponding conductor component 58 of connector assembly 500.

Figure 6C:
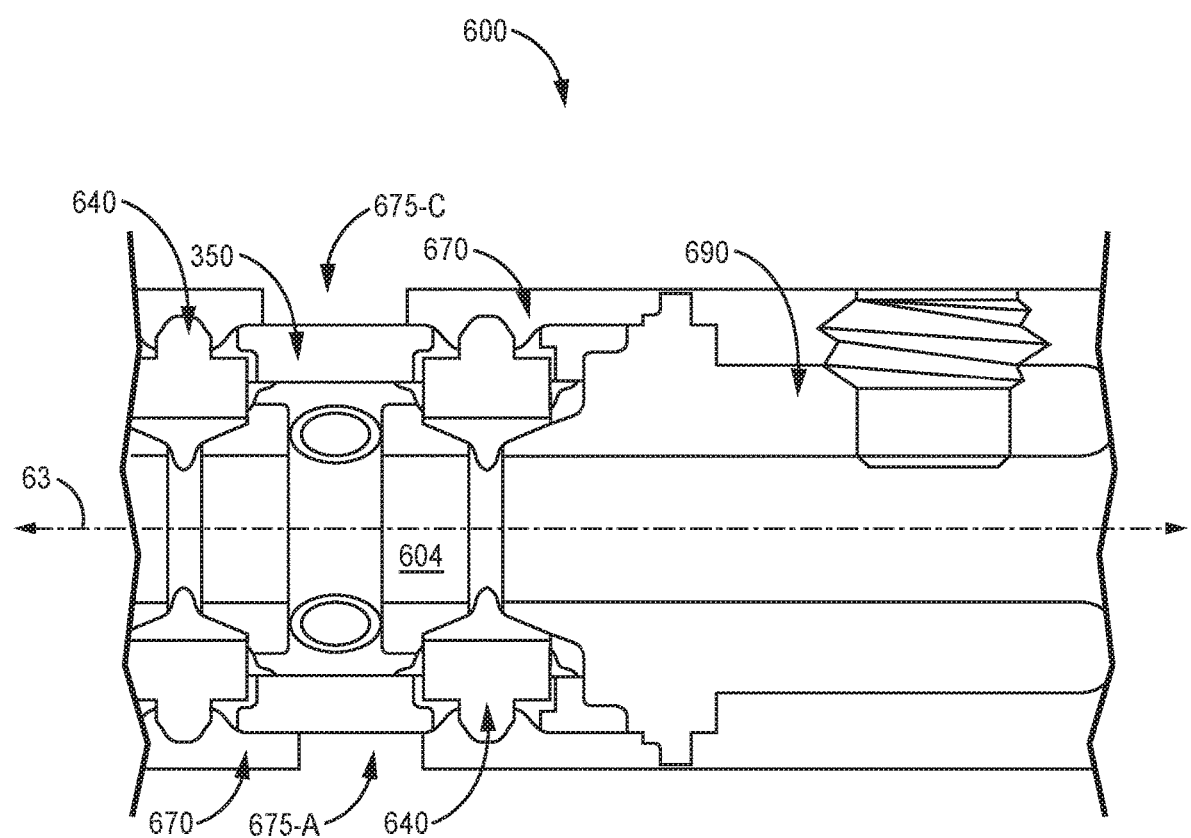
FIG. 6C is a longitudinal cross-section view through a portion of the assembly shown in FIGS. 6A-B, according to some embodiments.

FIGS. 6A-B are perspective views of opposing sides of the above-referenced female connector assembly 600, in which an alternative means for routing conductors 48 is provided by a flexible inner insulative sleeve 670. FIGS. 6A-B illustrate inner insulative sleeve 670 extending around the above described plurality of contact ring components 350 and an interspersed plurality of the aforementioned isolation ring components 640 (without guides) assembled together in-line, wherein each conductor component 48 (enumerated 48-1 through 48-8) extends within a corresponding longitudinally extending channel 677 of inner sleeve 670. Isolation ring components 640 can be seen in FIG. 6C, which is a longitudinal cross-section view through a portion of assembly 600. The plurality of longitudinally extending channels 677, each of which is formed in an outer surface of inner insulative sleeve 670, are shown extending substantially parallel to a longitudinal axis 63 of assembly 600 and being spaced apart from one another around the circumference of inner sleeve 670. An inner surface of inner insulative sleeve 670 is preferably in intimate contact with isolation ring components 640 and contact ring components 350, for example, having been insert molded thereabout, according to methods known in the art, from a flexible medical grade polymer such as silicone rubber. With reference back to FIG. 3A, assembly 600 may be integrated into extension 300, being contained within sleeve 320, in lieu of any of the above-described assemblies 400A, 400B, 500, such that a longitudinal axis 63 of assembly 600 (defined by a bore 604 of female connector assembly 600 seen in FIG. 6C) extends along a longitudinal axis 3 of sleeve 320, and distal terminal end 321 of sleeve 320 defines opening 301 into bore 604 of assembly 600. When isolation ring components 640, sleeve 320, and inner sleeve 670 are all formed from silicone rubber, the aforementioned desired flexibility of the length of extension 300 between male connector assembly 310 and distal terminal end 321 (FIG. 3A) is achieved; and, when sleeve 320 is insert molded around assembly 600 after inner sleeve 670 is molded around components 350 and 640, a durability and integrity of electrical isolation are ensured by coalescence of the silicone rubber material at the interfaces between inner sleeve 670 and isolation ring components 640, and between sleeves 320 and 370.

FIGS. 6A-B further illustrate each channel 677 of flexible inner insulative sleeve 670 extending from a proximal end 670P of sleeve 670 to a corresponding coupling aperture 675-C of a plurality thereof that are formed through sleeve 670, from the outer surface to the inner surface thereof. Each coupling aperture 675-C is shown positioned coincident with a corresponding contact ring component 350, and first end 481 of each conductor component 48-1, 48-2, 48-3, 48-4, 48-5, 48-6, 48-7, 48-8 is shown extending through one of apertures 675-C for coupling to the corresponding contact ring component 350, for example, by welding. According to some embodiments, inner insulative sleeve 670 may further include access apertures 675-A, each of which is positioned coincident with a corresponding contact ring component 350, and opposite a corresponding coupling aperture 675-C. Access apertures 675-A may provide a suitable interface for supports during the coupling of conductor component first ends 481 to contact ring components 350.

According to some methods, after inner insulative sleeve 670 is insert molded around the in-line assembly of components 640, 350, each conductor component 48 is positioned in the corresponding channel 677 and first end 481 of each is coupled, for example, welded, to the corresponding conductor ring component 350, either before or after a plurality of couplings 672 is formed. Each coupling 672 may be formed with a conductive sleeve that joins together each conductor component 48 and the corresponding elongate insulated conductor of the aforementioned plurality of elongate insulated conductors of extension 300 (shown with dashed lines in FIG. 3A), for example, by crimping, welding or any other suitable method known to those skilled in the art. With further reference to FIGS. 6A-B, each coupling 672 is shown located in a corresponding channel 677, at proximal end 670P of inner sleeve 670, and proximal end 670P preferably tapers in a proximal direction to a smaller diameter. After coupling each conductor component first end 481 and forming each of couplings 672, insulative sleeve 320 can be insert molded around assembly 600 while channels 677 of inner sleeve 670 hold the lengths of conductor components 48 and couplings 672 in place. In some preferred embodiments, channels 677 may be dimensioned to provide a compression or friction fit of conductor components 48 therein; and, according to some embodiments and methods, to further constrain conductor components 48 from moving out of line from channels 677 during the molding of sleeve 320, one or more silicone rubber bands may each be fitted in a corresponding optional circumferential groove 678, so that each band extends over components 48. FIGS. 6A-B show inner sleeve 670 including three circumferential grooves 678 formed in the outer surface thereof and spaced apart from one another in proximity to proximal end 670P. Note that one such band is represented with dashed lines in FIG. 6A, being fitted with the groove 678 that is closest to proximal end 670P.

Finally, FIGS. 6A-C show female connector assembly 600 including a set-screw component 690, known to those skilled in the art, which is located within a distal end 670D of flexible inner insulative sleeve 670, being in-line with isolation ring components 640 and contact ring components 350. According to the illustrated embodiment, set-screw component 690 is employed to retain the fully inserted lead terminal connector 21. It should be noted that any of the other female connector assemblies 400A, 400B, 500 may be integrated together with a set-screw component, like set-screw component 679, when contained in insulative sleeve 320 (FIG. 3A).

In the foregoing detailed description, the disclosure has been described with reference to specific embodiments. However, it may be appreciated that various modifications and changes can be made without departing from the scope of the disclosure as set forth in the appended claims. For instance, while the foregoing describes the connector assembly mechanisms as coupling an extension and a lead for a medical system, it may be used to couple other components of a medical system. Furthermore various combinations of elements described above in conjunction with the specific embodiments, are within the scope of the present disclosure, for example, according to the following statements:

1. A female connector assembly to be contained in an insulative sleeve, a bore of the assembly defining a longitudinal axis of the assembly, an opening into the bore being formed by a distal terminal end of the sleeve, when the assembly is contained therein, and the assembly comprising:
   a plurality of isolation ring components spaced apart from one another along a length of the assembly, each isolation ring component of the plurality having an outer surface and an inner surface, the inner surface defining a portion of the bore, each portion of the bore extending from a first end of the corresponding isolation ring component to a second end of the corresponding isolation ring component along the longitudinal axis, and each isolation ring component comprising a seal lip extending into the bore, the lip being defined by the inner surface, the seal lip being spaced apart from the first end along the longitudinal axis;
   a plurality of contact ring components spaced apart from one another along a length of the assembly, each contact ring component of the plurality extending around the bore, being interspersed among the plurality of isolation ring components; and
   a plurality of conductor components, each conductor component of the plurality having a curvature formed therein along a length thereof, each conductor component having a first end coupled to a corresponding contact ring component, and the length of each conductor component extending proximally from the coupled first end, and into a proximal portion of the insulative sleeve, when the assembly is contained in the sleeve.

2. The assembly of statement 1, wherein the curvature of each conductor component is defined by a helix.

3. The assembly of statement 2, wherein a centerline of the helix of each conductor component is laterally offset from the longitudinal axis.

4. The assembly of statement 2, wherein the longitudinal axis substantially defines a centerline of the helix of each conductor component.

5. The assembly of statement 1, wherein the curvature of each conductor component is defined by a repeating sigmoid.

6. The assembly of any one of statements 1-5, wherein:
   each isolation ring component further comprises a guide extending outward from the outer surface, the guide having a channel formed therethrough, the channel extending substantially parallel to the longitudinal axis from a first opening thereof to a second opening thereof, the first opening being located in proximity to the first end; and
   the length of each conductor component extends through the guide channel of at least one of the plurality of isolation ring components.

7. The assembly of statements 6, wherein the guide channels of the isolation ring components are aligned with one another along the longitudinal axis, and the length of a first conductor component of the plurality of conductor components extends through each guide channel.

8. The assembly of statement 6, wherein the guide channels of the isolation ring components are circumferentially offset from one another around the longitudinal axis, and the length of a first conductor component of the plurality of conductor components extends through each guide channel.

9. An extension comprising a female connector assembly according to any of the statements 1-8, the insulative sleeve containing the female connector assembly, a male connector assembly, and a plurality of elongate insulated conductors extending therebetween, the male connector assembly including a plurality of external contacts spaced apart from one another along a length of the male connector assembly, each elongate insulated conductor including a proximal end and a distal end, the proximal end being electrically coupled to a corresponding contact of the female connector assembly, and the distal end being electrically coupled to the female connector assembly.

10. The extension of statement 9, wherein each conductor component of the plurality of conductor components of the female connector assembly is an integral extension of a corresponding elongate insulated conductor, such that the coupled first end of each conductor component comprises a distal end of the corresponding elongate insulated conductor.

11. A female connector assembly to be contained in a flexible outer insulative sleeve, a bore of the assembly defining a longitudinal axis of the assembly, an opening into the bore being formed by a distal terminal end of the outer sleeve, when the assembly is contained therein, and the connector assembly comprising:
   a plurality of isolation ring components spaced apart from one another along a length of the assembly, each isolation ring component of the plurality extending around the bore and each having an inner surface that defines a seal lip extending into the bore;
   a plurality of contact ring components spaced apart from one another along a length of the assembly, each contact ring component of the plurality extending around the bore, being interspersed among the plurality of isolation ring components; and
   a plurality of conductor components, each conductor component of the plurality of conductor components having a curvature formed therein along a length thereof, a first end of each conductor component being coupled to a corresponding contact ring component, and the length of each conductor component extending proximally from the coupled first end into a proximal portion of the outer insulative sleeve.

12. The assembly of statement 11, wherein the curvature of each conductor component is defined by a repeating sigmoid.

13. The assembly of statement 11, wherein the curvature of each conductor component is defined by a helix, a centerline of the helix of each conductor component being laterally offset from the longitudinal axis.

14. The assembly of any of statements 11-13, further comprising:
a flexible inner insulative sleeve extending around the pluralities of isolation ring components and contact ring components and along the length of the assembly, from a proximal end thereof to a distal end thereof, such that an inner surface of the inner insulative sleeve is in intimate contact with each of the isolation ring and contact ring components, the inner sleeve including a plurality of longitudinally extending channels formed in an outer surface thereof and a plurality of apertures formed therethrough, from the outer surface to the inner surface, each aperture of the plurality of apertures being coincident with a corresponding contact ring component, the plurality of channels extending substantially parallel to the longitudinal axis and being spaced apart from one another around the circumference of the inner sleeve, and each channel of the plurality of channels extending from the proximal end of the inner sleeve to a corresponding aperture; and
wherein each conductor component extends in a corresponding channel of the plurality of channels of the inner sleeve; and
the first end of each conductor component extends through a corresponding aperture of the plurality of apertures of the inner sleeve.

15. The assembly of statement 14, further comprising a band extending over the plurality of conductor components, and wherein the inner sleeve further includes a circumferential groove formed in the outer surface thereof and located in proximity to the proximal end of the inner sleeve, the band being fitted in the groove.

16. An extension comprising a female connector assembly according to any of the statements 11-15, the outer insulative sleeve containing the female connector assembly, a male connector assembly, and a plurality of elongate insulated conductors extending therebetween, the male connector assembly including a plurality of external contacts spaced apart from one another along a length of the male connector assembly, each elongate insulated conductor including a proximal end and a distal end, the proximal end being electrically coupled to a corresponding contact of the female connector assembly, and the distal end being electrically coupled to the female connector assembly.

17. The extension of statement 16, wherein each conductor component of the plurality of conductor components of the female connector assembly is an integral extension of a corresponding elongate insulated conductor, such that the coupled first end of each conductor component comprises a distal end of the corresponding elongate insulated conductor.

18. The extension of statement 16, further comprising:
a plurality of couplings, each coupling being between one of the plurality of elongate insulated conductors and a corresponding conductor component; and wherein the proximal end of the flexible inner insulative sleeve tapers in a proximal direction to a smaller diameter; and
each coupling is located at the proximal end of the inner sleeve and in a corresponding channel of the plurality of channels thereof.

19. An implantable medical electrical system comprising a device, a lead, and an extension, according to any of statements 9, 10, and 16-18, for electrically coupling the lead to the device, the device being configured to deliver electrical impulses through an array of electrodes mounted to the lead.

20. An isolation ring component for inclusion in a female connector assembly, the assembly further comprising an elongate conductor component and a contact ring component, the isolation ring component having an outer surface and an inner surface, the inner surface defining a bore, the bore extending from a first end of the isolation ring component to a second end of the isolation ring component along a longitudinal axis thereof, and the isolation ring component comprising:
an annular groove formed in a face of the first end such that the groove extends around the longitudinal axis, the groove being configured to engage with an end of the contact ring component;
an integrally formed guide extending outward from the outer surface, the guide having a channel formed therethrough, the channel extending from a first opening thereof to a second opening thereof and substantially parallel to the longitudinal axis, the first opening being formed in the face of the first end, and the channel being configured to receive extension of the elongate conductor component therethrough, from the first opening to the second opening; and
an integrally formed seal lip extending into the bore, the lip being defined by the inner surface, the seal lip being spaced apart from the face of the first end, and apart from the annular groove, along the longitudinal axis.

21. The isolation ring component of statement 20, wherein the guide comprises a plurality of lobes, and the channel is one of a plurality of channels of the guide, each channel of the plurality of channels being formed through a corresponding lobe of the guide.

22. An isolation ring component for inclusion in a female connector assembly, the assembly further comprising an elongate conductor component and a contact ring component, the isolation ring component having an outer surface and an inner surface, the inner surface defining a bore, the bore extending from a first end of the isolation ring component to a second end of the isolation ring component along a longitudinal axis thereof, and the isolation ring component comprising:
an annular groove formed in a face of the first end such that the groove extends around the longitudinal axis, the groove being configured to engage with an end of the contact ring component; an integrally formed guide extending outward from the outer surface, the guide having a channel formed therethrough, the channel extending from a first opening thereof to a second opening thereof and substantially parallel to the longitudinal axis, the first opening being formed in the face of the first end, and the channel being configured to receive extension of the elongate conductor component therethrough, from the first opening to the second opening; and
an integrally formed seal lip extending into the bore, the lip being defined by the inner surface, the seal lip being spaced apart from the face of the first end, and apart from the annular groove, along the longitudinal axis.

23. The isolation ring component of statement 22, wherein the guide comprises a plurality of lobes, and the channel is one of a plurality of channels of the guide, each channel of the plurality of channels being formed through a corresponding lobe of the guide.

The invention claimed is:

1. A medical device comprising a connector assembly contained in a sleeve, the connector assembly comprising:
   a plurality of isolation ring components spaced apart from one another along a length of the connector assembly, each isolation ring component of the plurality having an outer surface and an inner surface, the inner surface defining a portion of a bore extending substantially along a longitudinal axis of the sleeve, each portion of the bore extending from a first end of the corresponding isolation ring component to a second end of the corresponding isolation ring component along the longitudinal axis, and each isolation ring component comprising:
   an annular groove formed in a face of the first end such that the groove extends around the longitudinal axis;
   a guide extending outward from the outer surface, the guide having a channel formed therethrough, the channel extending substantially parallel to the longitudinal axis from a first opening thereof to a second opening thereof, the first opening being located in proximity to the face of the first end; and
   a seal lip extending into the bore, the lip being defined by the inner surface, the seal lip being spaced apart from the face of the first end, and apart from the annular groove, along the longitudinal axis;
   a plurality of contact ring components spaced apart from one another along a length of the connector assembly, each contact ring component of the plurality extending around the bore, being interspersed among the plurality of isolation ring components, and each contact ring component having an end engaged within the annular groove of a corresponding isolation ring component; and
   a plurality of conductor components, each conductor component of the plurality having a curvature formed therein along a length thereof, each conductor component having a first end coupled to a corresponding contact ring component, and the length of each conductor component extending from the coupled first end, through the guide channel of at least one of the plurality of isolation ring components, and into a proximal portion of the insulative sleeve.

2. The medical device of claim 1, wherein the curvature of each conductor component is defined by a repeating sigmoid.

3. The medical device of claim 1, wherein the curvature of each conductor component is defined by a helix.

4. The medical device of claim 3, wherein the longitudinal axis substantially defines a centerline of the helix of each conductor component.

5. The medical device of claim 3, wherein a centerline of the helix of each conductor component is laterally offset from the longitudinal axis.

6. The medical device of claim 1, wherein the guide channels of the isolation ring components are aligned with one another along the longitudinal axis, and the length of a first conductor component of the plurality of conductor components extends through each guide channel.

7. The medical device of claim 6, wherein the curvature of each conductor component is defined by a repeating sigmoid.

8. The medical device of claim 6, wherein the curvature of each conductor component is defined by a helix.

9. The medical device of claim 1, wherein the guide channels of the isolation ring components are circumferentially offset from one another around the longitudinal axis, and the length of a first conductor component of the plurality of conductor components extends through each guide channel, such that the curvature of each conductor component is defined by a helix having a centerline substantially defined by the longitudinal axis.

10. A medical system comprising an assembly, the assembly comprising:
    a plurality of isolation ring components spaced apart from one another along a length of the assembly, the assembly comprising a bore and the bore defining a longitudinal axis of the assembly, each isolation ring component of the plurality extending around the bore and each having a surface that defines a seal lip extending into the bore;
    a plurality of contact ring components spaced apart from one another along the length of the assembly, each contact ring component of the plurality extending around the bore, being interspersed among the plurality of isolation ring components; and
    a plurality of conductor components, each conductor component of the plurality of conductor components having a curvature formed therein along a length thereof, wherein the curvature of each conductor component is defined by one of a repeating sigmoid or a helix, the helix having a centerline laterally offset from the longitudinal axis, a first end of each conductor component being coupled to a corresponding contact ring component, and the length of each conductor component extending proximally from the first end.

11. The medical system of claim 10, further comprising:
    a flexible inner insulative sleeve extending around the pluralities of isolation ring components and contact ring components and along the length of the assembly, from a proximal end thereof to a distal end thereof, such that an inner surface of the inner insulative sleeve is in intimate contact with each of the isolation ring and contact ring components, the inner sleeve including a plurality of longitudinally extending channels formed in an outer surface thereof and a plurality of apertures formed therethrough, from the outer surface to the inner surface, each aperture of the plurality of apertures being coincident with a corresponding contact ring component, the plurality of channels extending substantially parallel to the longitudinal axis and being spaced apart from one another around the circumference of the inner insulative sleeve, and each channel of the plurality of channels extending from the proximal end of the inner insulative sleeve to a corresponding aperture; and
    wherein each conductor component extends in a corresponding channel of the plurality of channels of the inner insulative sleeve; and
    the first end of each conductor component extends through a corresponding aperture of the plurality of apertures of the inner insulative sleeve.

12. The medical system of claim 11, further comprising a band extending over the plurality of conductor components, and wherein the inner sleeve further includes a circumferential groove formed in the outer surface thereof and located in proximity to the proximal end of the inner sleeve, the band being fitted in the groove.

13. The medical system of claim 10, further comprising:
an implantable medical device; and
an extension coupled to the implantable medical device, the extension comprising the plurality of isolation ring components, the plurality of contact ring components, and the plurality of conductor components.

14. A medical device comprising a female connector assembly and a male connector assembly, the male connector assembly including a plurality of external contacts spaced apart from one another along a length of the male connector assembly, each contact of the male connector assembly being electrically coupled to the female connector assembly, the female connector assembly being contained in a flexible outer insulative sleeve, a bore of the female connector assembly extending along a longitudinal axis of the outer sleeve, and an opening into the bore being formed by a distal terminal end of the outer sleeve, and the female connector assembly comprising:
a plurality of isolation ring components spaced apart from one another along a length of the assembly, each isolation ring component of the plurality extending around the bore and each having an inner surface that defines a seal lip extending into the bore;
a plurality of contact ring components spaced apart from one another along a length of the assembly, each contact ring component of the plurality extending around the bore, being interspersed among the plurality of isolation ring components; and
a plurality of conductor components, each conductor component of the plurality of conductor components having a curvature formed therein along a length thereof, wherein the curvature of each conductor component is defined by one of a repeating sigmoid or a helix, the helix having a centerline laterally offset from the longitudinal axis, a first end of each conductor component being coupled to a corresponding contact ring component, and the length of each conductor component extending proximally from the coupled first end into a proximal portion of the outer insulative sleeve.

15. The medical device of claim 14, wherein each conductor component of the plurality of conductor components of the female connector assembly comprises a distal portion of an elongate insulated conductor, a proximal end of the elongate insulated conductor being electrically coupled to a corresponding contact of the male connector assembly.

16. The medical device of claim 14, wherein the female connector assembly further comprises:
a flexible inner insulative sleeve extending around the pluralities of isolation ring components and contact ring components and along the length of the assembly, from a proximal end thereof to a distal end thereof, such that an inner surface of the inner insulative sleeve is in intimate contact with each of the isolation ring and contact ring components, the inner sleeve including a plurality of longitudinally extending channels formed in an outer surface thereof and a plurality of apertures formed therethrough, from the outer surface to the inner surface, each aperture of the plurality of apertures being coincident with a corresponding contact ring component, the plurality of channels extending substantially parallel to the longitudinal axis and being spaced apart from one another around the circumference of the inner sleeve, and each channel of the plurality of channels extending from the proximal end of the inner sleeve to a corresponding aperture; and
wherein each conductor component extends in a corresponding channel of the plurality of channels of the inner sleeve; and
the first end of each conductor component extends through a corresponding aperture of the plurality of apertures of the inner sleeve.

17. The medical device of claim 16, wherein the connector assembly further comprises a band extending over the plurality of conductor components, and the inner sleeve of the assembly further includes a circumferential groove formed in the outer surface thereof and located in proximity to the proximal end of the inner sleeve, the band being fitted in the groove.

18. The medical device of claim 16, further comprising:
a plurality of couplings, each coupling being between one of the plurality of elongate insulated conductors and a corresponding conductor component; and
wherein the proximal end of the flexible inner insulative sleeve tapers in a proximal direction to a smaller diameter; and
each coupling is located at the proximal end of the inner sleeve and in a corresponding channel of the plurality of channels thereof.

19. An implantable medical system comprising:
an implantable medical device configured to deliver therapy to a patient;
a lead; and
an extension configured to electrically couple the lead to the implantable medical device, the extension comprising a female connector assembly and a male connector assembly, the male connector assembly comprising a plurality of external contacts spaced apart from one another along a length of the male connector assembly, each contact of the male connector assembly being electrically coupled to the female connector assembly, the female connector assembly being contained in a flexible outer insulative sleeve, a bore of the female connector assembly extending along a longitudinal axis of the outer sleeve, and an opening into the bore being formed by a distal terminal end of the outer sleeve, and the female connector assembly comprising:
a plurality of isolation ring components spaced apart from one another along a length of the assembly, each isolation ring component of the plurality extending around the bore and each having an inner surface that defines a seal lip extending into the bore;
a plurality of contact ring components spaced apart from one another along a length of the assembly, each contact ring component of the plurality extending around the bore, being interspersed among the plurality of isolation ring components; and
a plurality of conductor components, each conductor component of the plurality of conductor components having a curvature formed therein along a length thereof, wherein the curvature of each conductor component is defined by one of a repeating sigmoid or a helix, the helix having a centerline laterally offset from the longitudinal axis, a first end of each conductor component being coupled to a corresponding contact ring component, and the length of each conductor component extending proximally from the coupled first end into a proximal portion of the outer insulative sleeve.

20. The system of claim 19, wherein each conductor component of the plurality of conductor components of the female connector assembly of the extension comprises a distal portion of an elongate insulated conductor, a proximal end of the elongate insulated conductor being electrically coupled to a corresponding contact of the male connector assembly.

* * * * *